(12) United States Patent  
Palti

(10) Patent No.: US 9,146,230 B2
(45) Date of Patent: Sep. 29, 2015

(54) CONTINUOUS MONITORING OF GLUCOSE AND OTHER LIVING BODY CONSTITUENTS

(76) Inventor: Yoram Palti, Haifa (IL)

( * ) Notice: Subject to any disclaimer, the term of this patent is extended or adjusted under 35 U.S.C. 154(b) by 615 days.

(21) Appl. No.: 13/527,708

(22) Filed: Jun. 20, 2012

(65) Prior Publication Data

US 2012/0323094 A1 Dec. 20, 2012

Related U.S. Application Data

(60) Provisional application No. 61/498,854, filed on Jun. 20, 2011.

(51) Int. Cl.
 A61B 5/1455 (2006.01)
 G01N 33/50 (2006.01)
 A61B 5/1459 (2006.01)
 A61B 5/145 (2006.01)
 A61B 5/00 (2006.01)
 G01N 33/66 (2006.01)

(52) U.S. Cl.
 CPC .......... *G01N 33/5073* (2013.01); *A61B 5/1459* (2013.01); *A61B 5/14532* (2013.01); *A61B 5/686* (2013.01); *G01N 33/66* (2013.01)

(58) Field of Classification Search
 CPC ............. A61B 5/14532; A61B 5/1455; A61B 5/1459; A61B 5/686
 See application file for complete search history.

(56) References Cited

U.S. PATENT DOCUMENTS 5,101,814 A * 4/1992 Palti .............................. 600/347
5,368,028 A 11/1994 Palti
2001/0017649 A1 8/2001 Yaron
2005/0136092 A1 * 6/2005 Rotem et al. .................. 424/423
2007/0249007 A1 10/2007 Rosero

FOREIGN PATENT DOCUMENTS

EP 2009095 12/2008
WO 91/01680 2/1991

OTHER PUBLICATIONS

Valiunas V, Doronin S, Valiuniene L, Potapova I, Zuckerman J, Walcott B, Robinson RB, Rosen MR, Brink PR, Cohen IS: Human mesenchymal stem cells make cardiac connexins and form functional gap junctions. J Physiol. 2004: 555: 617-626.
Valiunas V, Polosina YY, Miller H, Potapova IA, Valiuniene L, Doronin S, Mathias RT, Robinson RB, Rosen MR, Cohen IS, Brink PR. Connexin-specific cell-to-cell transfer of short interfering RNA by gap junctions. J Physiol. 2005;568:459-68.

(Continued)

*Primary Examiner* — Eric Winakur
(74) *Attorney, Agent, or Firm* — Proskauer Rose LLP

(57) ABSTRACT

Methods and apparatuses for monitoring the level of glucose or other constituents in live subjects are disclosed. Stem cells are obtained from the subject and processed into cells that change their optical characteristics in response to a level of the constituent. The responsive cells are formed into clusters and implanted into in the subject's body at locations that permit optical monitoring from outside the subject's body. The implanted cell clusters are illuminated and the reflected illumination from each of the cell clusters is detected. Changes in the optical characteristics of the cell clusters that correspond to the responses of the cell clusters are identified, and the identified changes are mapped to a constituent level based on calibration data for each cell cluster. An indication of the constituent level in the subject is then output.

21 Claims, 4 Drawing Sheets

(56) References Cited

OTHER PUBLICATIONS

Valiunas V, Kanaporis G, Valiuniene L, Gordon C, Wang HZ, Li L, Robinson RB, Rosen MR, Cohen IS, Brink PR. Coupling an HCN2-expressing cell to a myocyte creates a two-cell pacing unit. J Physiol. 2009:587: 5211-26.

Potapova I, Plotnikov A, Lu Z, Danilo P Jr, Valiunas V, Qu J, Doronin S, Zuckerman J, Shlapakova IN, Gao J, Pan Z, Herron AJ, Robinson RB, Brink PR, Rosen MR, Cohen IS: Human mesenchymal stem cells as a gene delivery system to create cardiac pacemakers. Circ Res 94:952-959, 2004.

Plotnikov AN, Shlapakova I, Szabolcs MJ, Danilo Jr P, Lorell BH, Potapova IA, Lu Z, Rosen AB, Mathias RT, Brink PR, Robinson RB, Cohen IS, Rosen MR. Xenografted adult human mesenchymal stem cells provide a platform for sustained biological pacemaker function in canine heart. Circulation 2007;116:706-713.

Aggarwal S, Pittenger MF. Human mesenchymal stem cells modulate allogeneic immune cell responses. Blood. 2005;105:1815-1822.

Rosen MR. Are Stem Cells Drugs? The regulation of stem cell research and development. Circulation. 2006;114:1992-2000.

Christini DJ, Walden J, Edelberg JM. Direct biologically based biosensing of dynamic physiological function. Am J Physiol Heart Circ Physiol. 2001:280.:H2006-10.

Edelberg JM, Jacobson JT, Gidseg DS, Tang L, Christini DJ. Enhanced myocyte-based biosensing of the blood-borne signals regulating chronotropy. J Appl Physiol. 2002:92:581-585.

Novak A, Shtrichman R, Germanguz I, Segev H, Zeevi-Levin N, Fishman B, Mandel YE, Barad L, Domev H, Kotton D, Mostoslaysky G, Binah O, Itskovitz-Eldor J. Enhanced reprogramming and cardiac differentiation of human keratinocytes derived from plucked hair follicles, using a single excisable lentivirus. Cell Reprogram. 2010;12:665-78.

Palti Y., David G.B., Lachov E., Mika Y.H. and Schatzberger R. Islets of Langerhans generate electric activity modulated by glucose concentration. Diabetes 45: 595-601 (1996).

Cohen L. B. Changes in Neuron Structure During Action Potential Propagation and Synaptic Transmission. Physiological Reviews 1973; 53:373-418.

Benedikt W. Graf, Tyler S. Ralston, Han-Jo Ko, and Stephen A. Boppart Detecting intrinsic scattering changes correlated to neuron action potentials using optical coherence imaging. Optics Express 2009; 17: 13447-13457.

B. J. Baker, E. K. Kosmidis, D. Vucinic, C. X. Falk, L. B. Cohen, M. Djurisic, and D. Zecevic Imaging brain activity with voltage—and calcium-sensitive dyes.• Cell. Mol. Neurobiol. 2005; 25:245-282.

R. A. Stepnoski, A. LaPorta, F. Raccuia-Behling, G. E. Blonder, R. E. Slusher, and D. Kleinfeld Noninvasive detection of changes in membrane potential in cultured neurons by light scattering.• Proc. Natl. Acad. Sci. U.S.A. 1991; 88:9382-386.

K. Holthoff and O. W. Witte, Intrinsic optical signals in rat neocortical slices measured with near-infrared dark-field microscopy reveal changes in extracellular space 1996; J. Neurosci. 16: 2740-2749.

R. U. Maheswari, H. Takaoka, H. Kadono, R. Homma, and M. Tanifuji, Novel functional imaging technique from brain surface with optical coherence tomography enabling visualization of depth resolved functional structure in vivo 2003;• J. Neurosci. Methods 124: 83-92.

T. Akkin, D. P. Dave, T. E. Milner, and H. Rylander 2004; Detection of neural activity using phase-sensitive optical low-coherence reflectometry Opt. Express 12: 2377-2386.

T. Akkin, C. Joo, and J. F. de Boer, Depth-resolved measurement of transient structural changes during action potential propagation 2007; Biophys. J. 93: 1347-1353.

V. J. Srinivasan, M. Wojtkowski, J. G. Fujimoto, and J. S. Duker, In vivo measurement of retinal physiology with high-speed ultrahigh-resolution optical coherence tomography 2006; Opt. Lett.: 31, 2308-2310.

J. F. de Boer, T. E. Milner, M. J. van Gernert, and J. S. Nelson Two-dimensional birefringence imaging in biological tissue by polarization-sensitive optical coherence tomography 1997;• Opt. Lett.: 22, 934-936.

Akkin T, Landowne D, Sivaprakasam A. Detection of Neural Action Potentials Using Optical Coherence Tomography: Intensity and Phase Measurements with and without Dyes. 2010; Front Neuroenergetics:6, 2-22.

Li Y, Gonzalez S, Terwey TH, Wolchok J, Li Y, Aranda I, Toledo-Crow R, Halpern AC Dual mode reflectance and fluorescence confocal laser scanning microscopy for in vivo imaging melanoma progression in murine skin. 2005; Invest Dermatol. 125:798-804.

Shan Jiang, Muthu Kumara Gnanasammandhan and Yong Zhang Optical imaging-guided cancer therapy with fluorescent nanoparticles 2010; J. R. Soc. Interface 7: 3-18.

Xiaoxiao He, Kemin Wang, Zhen Cheng 2010; In vivo near—infrared fluorescence imaging of cancer with nanoparticle—based probes 2010; Wiley Interdisciplinary Reviews: Nanomedicine and Nanobiotechnology vol. 2:349-366.

James R. Mansfield, Clifford C. Hoyt, Peter J. Miller, and Richard M. Levenson Distinguished photons: increased contrast with multispectral in vivo fluorescence imaging 2005; BioTechniques:39: S33-S37.

Wild, S, Roglic, G, Green, a, et al. Global prevalence of diabetes: estimates for the year 2000 and projections for 2030. Diabetes Care 2004; 27:1047.

Intensive blood-glucose control with sulphonylureas or insulin compared with conventional treatment and risk of complications in patients with type 2 diabetes (UKPDS 33). UK Prospective Diabetes Study (UKPDS) Group. Lancet 1998; 352:837.

Humphrey, LL, Ballard, DJ, Frohnert, PP, et al. Chronic renal failure in non-insulin-dependent diabetes mellitus. A population-based study in Rochester, Minnesota. Ann Intern Med 1989; 111:788.

Edelberg, Jay M et al: "Enhanced myocyte-based biosensing of the blood-borne signals regulating chronotropy." Journal of Applied Physiology, vol. 92, No. 2, Feb. 2002, pp. 581-585.

Kroon, Evert et al; "Pancreatic endoderm derived from human embryonic stem cells generates glucose-responsive insulin-secreting cells in vivo", Nature Biotechnology, vol. 26, No. 4, Apr. 1, 2008, pp. 443-452.

Search Report and Written Opinion from corresponding application PCT/IB2012/001228.

Moss, S.E. et al., "The incidence of vision loss in a diabetic population." Ophthalmology, Oct. 1988, 95(10):1340-8 (abstract only).

Chelluri, Lakshmi Kiran et al., Improved differentiation protocol of rat bone marrow precursors to functional islet like cells. Transplant Immunology & Stem Cell Lab., Stem Cell Studies Mar. 2, 2011; vol. 1:e5 pp. 36-41.

* cited by examiner

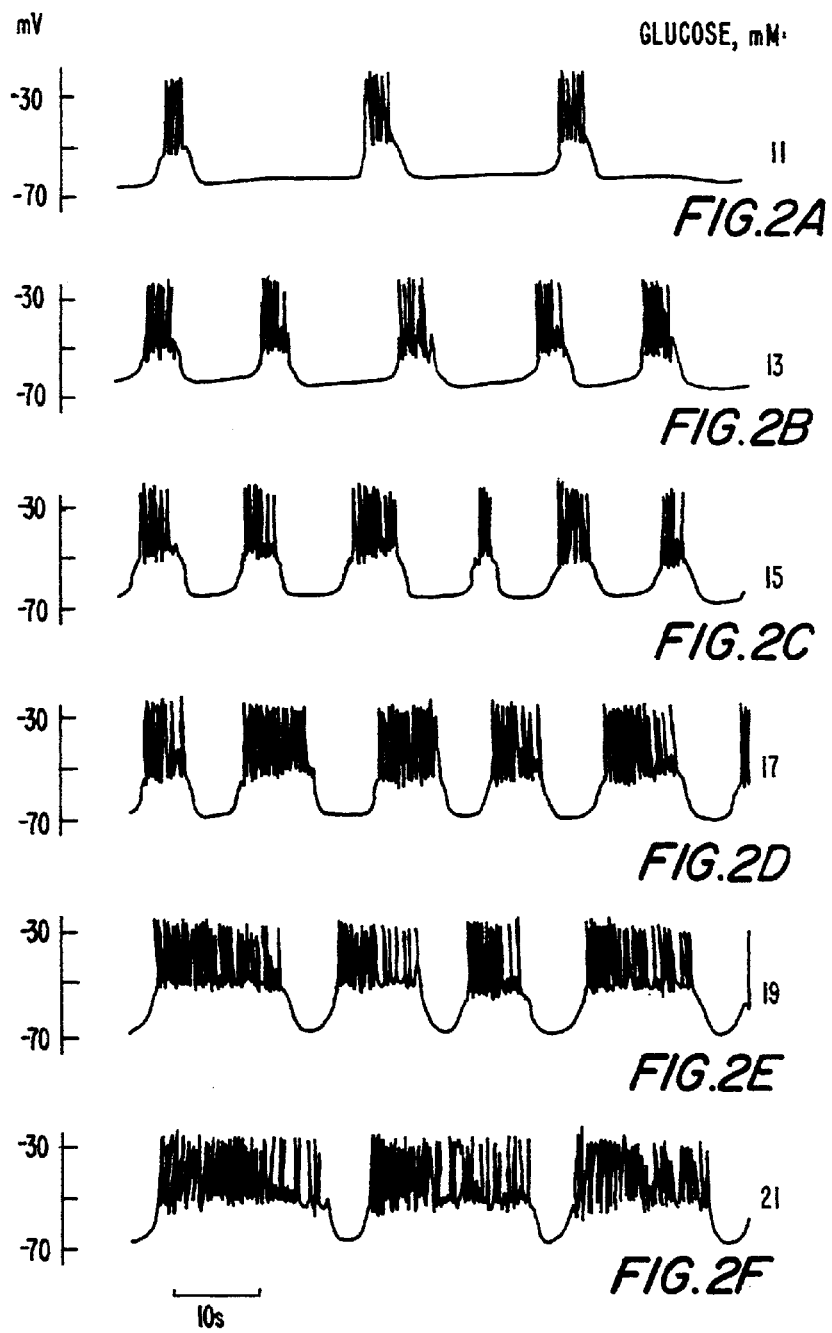

US 9,146,230 B2

CONTINUOUS MONITORING OF GLUCOSE AND OTHER LIVING BODY CONSTITUENTS

CROSS REFERENCE TO RELATED APPLICATIONS

This Application claims the benefit of U.S. Provisional Application 61/498,854, filed Jun. 20, 2011, which is incorporated herein by reference.

BACKGROUND

1. Field of the Invention

The present invention relates to a minimally invasive, continuous monitoring technology for monitoring the concentration of body constituents, which can be useful to help maintain a person's or animal's well being and for treating certain diseases. Notable examples of constituents that may be monitored include: blood glucose, oxygenated hemoglobin, electrolytes, drug and toxic agent levels, bilirubin, etc.

For simplicity, the invention is described in the context of monitoring of blood glucose concentration. However, the invention can be similarly used for monitoring the concentrations of other body constituents.

2. Background of Glucose Monitoring

Diabetes is the fastest growing serious illness in the western world. In the US and Europe there are well over 40 million people suffering from diabetes (see reference #1, identified below). Diabetes that is characterized by elevated blood glucose levels is associated with numerous severe pathologies that are responsible for serious clinical manifestations in many of the body systems, for example, cardiovascular, neurological, renal, ophthalmic etc (see references #28-31, identified below). The unstable blood glucose level may also result in life threatening hypoglycemia.

Many of the medical complications associated with diabetes can be reduced and even prevented by strict control of the blood glucose level. However, this requires frequent measurement or monitoring of the blood glucose level and, on this basis, the introduction of the appropriate treatment. The treatment may range from diet to insulin injections or delivery by pumps. Unfortunately, conventional blood glucose concentration measurements require blood drawing. And because it is painful, many patients do not make the measurements as often as they should. As a result, they may not control their glucose level well enough and complications are quite common.

One prior art solution to this problem is to implant continuously monitoring sensors that are inserted into the body by means of a small bore needle (penetrating rather deep under the skin) and connected to an outside device by wire leads. But the use of such devices is thus far very limited.

SUMMARY OF THE INVENTION

One aspect of the invention is directed to a method of monitoring a glucose level in a live subject. In this method, at least one stem cell is obtained from the subject, and it is processed into a plurality of signal-generating cells that change their optical characteristics in response to changes in glucose concentration. The plurality of signal-generating cells are formed into at least two cell clusters. For each of the cell clusters, calibration data is that relates responses of the respective cell cluster to glucose levels is determined. The clusters are implanted into in the subject's body at locations that permit optical characteristics of the cell clusters to be detected from outside the subject's body after implantation. The clusters are then illuminated and the reflected illumination from each of the clusters is detected. Changes in the optical characteristics of the cell clusters that correspond to the responses of the cell clusters are identified for each of the cell clusters, based on changes in the amount of reflected illumination that was detected. For each of the clusters, the identified change in optical characteristics is mapped to a glucose level based on the calibration data for the respective cell cluster. An indication of the glucose level in the subject is then output.

Another aspect of the invention is directed to an apparatus for monitoring a glucose level in a live subject into which at least two cell clusters have been implanted at locations that permit optical characteristics of the cell clusters to be detected from outside the subject's body after implantation. The apparatus includes a light source that is oriented to shine illumination onto the implanted cell clusters when the apparatus is fastened in place in a vicinity of the implanted cell clusters. The apparatus also includes a memory that holds calibration data for the implanted cell clusters, an array of light sensors that are oriented to receive illumination reflected from the implanted cell clusters when the apparatus is fastened in place and generate intensity data, and a processor. The processor is programmed to perform the steps of (a) inputting the intensity data, (b) identifying activity in the cell clusters, for each of the implanted cell clusters, based on changes the intensity data, (c) mapping, for each of the implanted cell clusters, the identified activity to a glucose level based on the calibration data stored in the memory, and (d) outputting an indication of the glucose level in the subject based a result of the mapping.

Another aspect of the invention is directed to a method of monitoring a constituent level in a live subject. In this method, at least one stem cell is obtained from the subject. The at least one stem cell is processed into a plurality of cells that change their optical characteristics in response to a level of the constituent. The responsive cells are formed into at least two cell clusters. Prior to implantation, for each of the cell clusters, calibration data that relates responses of the respective cell cluster to constituent levels is determined. The cell clusters are implanted into in the subject's body at locations that permit optical characteristics of the cell clusters to be detected from outside the subject's body after implantation. The implanted cell clusters are illuminated and the reflected illumination from each of the cell clusters is detected. Changes in the optical characteristics of the cell clusters that correspond to the responses of the cell clusters are identified, for each of the cell clusters, based on changes in the amount of reflected illumination. For each of the cell clusters, the identified change in optical characteristics is mapped to a constituent level based on the calibration data for the respective cell cluster. An indication of the constituent level in the subject based the constituent levels obtained in the mapping step is then output.

Another aspect of the invention is directed to an apparatus for monitoring a constituent level in a live subject into which at least two cell clusters have been implanted at locations that permit optical characteristics of the cell clusters to be detected from outside the subject's body after implantation. The apparatus includes a light source that is oriented to shine illumination onto the implanted cell clusters when the apparatus is fastened in place in a vicinity of the implanted cell clusters. The apparatus also includes a memory that holds calibration data for the implanted cell clusters, an array of light sensors that are oriented to receive illumination reflected from the implanted cell clusters when the apparatus is fastened in place and generate intensity data, and a processor.

The processor is programmed to perform the steps of (a) inputting the intensity data, (b) identifying activity in the cell clusters, for each of the implanted cell clusters, based on changes the intensity data, (c) mapping, for each of the implanted cell clusters, the identified activity to a constituent level based on the calibration data stored in the memory, and (d) outputting an indication of the constituent level in the subject based a result of the mapping.

BRIEF DESCRIPTION OF THE DRAWINGS

FIG. 2 is a set of graphs that depict how the generator cells respond to different concentrations of glucose.

DESCRIPTION OF THE PREFERRED EMBODIMENTS

Figure 1A:
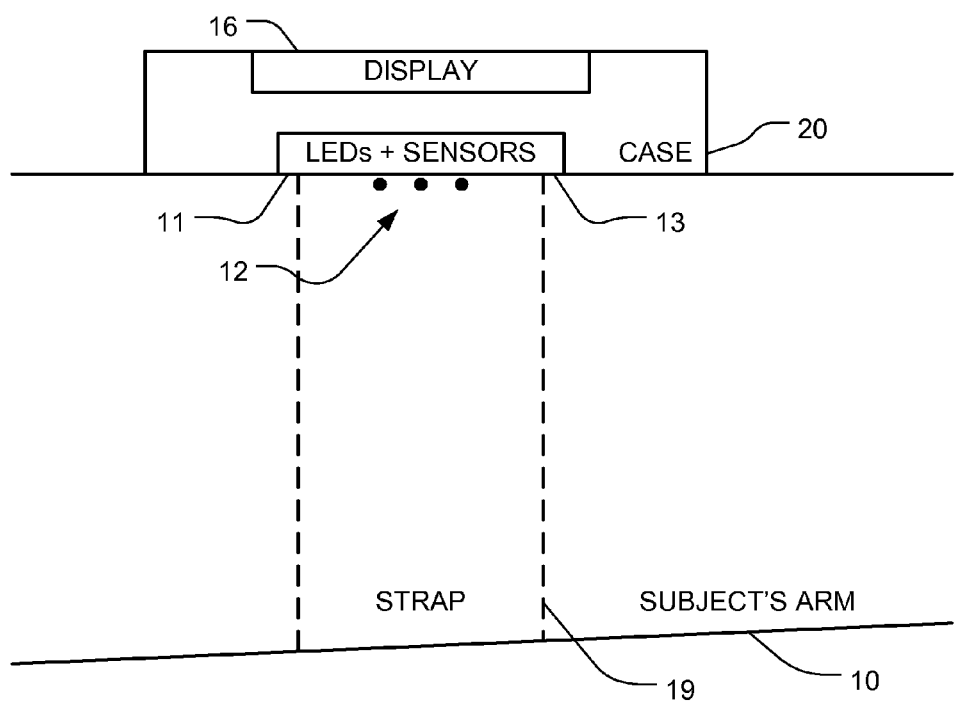
FIG. 1A is a schematic representation of a glucose measuring device, which is an embodiment of the present invention, in position on a subject's arm.

The preferred embodiments rely on the ability of specialized cells, such as the beta cells of the pancreas, to determine the glucose concentration in their environment and generate spikes, or action potentials, at a frequency proportional to the concentration. This effect is described in reference #11, which is identified below and incorporated herein by reference. Such cells are referred to herein as Generators, and devices that use such Generators are referred to herein as Glucoters.

Some preferred embodiments utilize genetically engineered adult human mesenchymal stem cells (hMSCs) that are engineered to express specific electrophysiological properties and provide electrical signals, as described in references #1-5, identified below. Specifically the cells are engineered to mimic the properties of pancreatic beta cells and to modulate the generation of pulses in response to the level of glucose that the cell is exposed to. By incorporation of the right connexins such Generator cells will form connexons that are induced to form gap junctions and function in synchrony with one another and, when so desired, with other types of cells to which they couple (see references #1-5). An inherent property of the hMSCs (which gives such cells an advantage over natural beta cells) is that they do not elicit an immune reaction when implanted allogeneically in experimental animals (see reference #5) as well as human subjects (see references #6 and 7, identified below).

When the above Generator cells express the proper connexins, form connexons, and form gap junctions with neighboring cells, they form clusters of cells in which the cells are electrically coupled and also can transmit between the cells small molecules of up to 24 base pairs (see references #2 and 3). In the context of glucose sensing, these clusters of Generators cells will form the equivalent of islets of Langerhans, and are therefore referred to herein as Sensor Islets, or SIs. In other contexts, the clusters of cells will sense constituents other than glucose.

Note that processing hMSCs into pseudo-beta cells, which have the capacity to sense glucose, is explained in reference #32, identified below. These pseudo-beta cells will respond to changes in external glucose concentration by changing the intracellular [Ca] and a spontaneous firing pattern, which normally leads to secretion of insulin. Either the intracellular [Ca] or the firing pattern can be used to provide an optical response that can be correlated with the extracellular glucose concentration.

The optimal size of the SIs for sensing glucose is believed to be 100-200µ. This optimum is due to the fact that, on the one hand the larger the GI the stronger the electric signal, while on the other the hand the diffusion of oxygen and nutrients is hampered in the large ensembles. (Note that this limitation does not apply to natural biological islets of Langerhans, because they are served by multiple blood vessels). The clusters can be grown to this size by allowing the cells to naturally aggregate into clumps. When the clusters reach the desired size, the clusters can be separated from each other and from individual cells, to prevent further aggregation.

Having induced to express (i.e. to activate the cell mechanisms that initiate the cellular production of selected proteins) the correct selection of connexins and ionic channels, the SIs synchronize by means of a functional pacemaker formed within them, similar to the way the natural islets do, as described in reference #11. By means of the pacemaker, the whole ensemble generates a wave of synchronized electric activity, as explained in reference #11. Furthermore, it was demonstrated that the frequency of these electric signals is proportional to the glucose concentration (see reference #11). These findings and concepts, as related to the naturally occurring islets of Langerhans are described in U.S. Pat. Nos. 5,101,814, 5,190,041, and 5,368,028, each of which is incorporated herein by reference.

Use of SIs to serve as glucose sensors was demonstrated in preliminary clinical trials, conducted by Carmel BioSensors, in which subcutaneously implanted gerbil islets, protected by a semipermeable membrane, produced electric spikes the frequency of which was proportional to the patient's blood glucose concentration (unpublished data). However, the Carmel BioSensors technology had two significant drawbacks: First, the semipermeable membrane interfered with oxygen and $CO_2$ diffusion thus compromising the cells' vitality. And second, the electric signals were conducted by leads, penetrating the skin, to an externally positioned electronic system. This configuration was necessary because the electric signals were too small to be picked up at the skin surface without using leads. Both of these drawbacks are avoided in the preferred embodiments described herein. First the protective capsule is no longer needed as the SIs are not recognized by the host immune system. Secondly, there is no need for the skin penetrating leads as the electric signals or spikes elicited by the Generators or SIs in response to glucose concentration can be monitored from the external skin surface. To achieve this, a variety of approaches for the signal generation configurations may be used.

In some preferred embodiments, the signal generation relies on Light scattering Generators (LSG): in these embodiments, the action potential waves generated in the SIs result in corresponding changes in their optic properties. These can result from both transient changes in membrane optic properties corresponding to the changes in the strength of the membrane electric field, as described in references #12, 13, and 15, each of which is identified below and incorporated herein by reference, and from minute cell volume and structural changes generated by the ion movements as described in references #12, 16, 19, identified below. These changes in the optic properties can be detected at a distance of a few mm (see references #14-18, 20, and 21, identified below). The changes in optic properties could include, for example, changes in the light scattering properties of the cells, or cell ensembles, involved. Thus, referring now to FIGS. 1A and 1B, when light is shined (e.g., from LEDs 11) through the skin onto the SIs 12, the changes in light scattering result in changes in the amount of light reaching an appropriate externally positioned optic sensor 13.

The LSG approach is currently the most preferred because it depends only on the Generator cells and does not require any additional elements (e.g., dyes that generate optic signals or semipermeable membranes that provide immune-protection the cells in the SIs). Note, however, that dyes may be implanted together with the SIs to make the SIs easier to locate from outside the subject's body.

In the preferred LSG approach, the SIs can be obtained by performing the following steps: First, stable hMSCs culture are obtained. A preferably source for the required stem cells is the subject into which the SIs will ultimately be implanted. One preferred source of such stem cells are hair follicles, as described in reference #10, identified below. Next, additional ionic channels (beyond the ones the cells already possess) are expressed in the hMSCs, as described in references #2-5. This results in an initial set of cells that are candidates for subsequent use.

Note that one suitable approach for obtaining the initial set of cells from a hair follicle is to fragment the follicle into individual cells. One or more stem cells are identified and isolated from the rest of the cells. The cells are processed by culturing them with appropriate factors that induce their differentiation to the desired cells type of cell (i.e., cells that respond to glucose in a manner similar to pancreatic beta cells). These cells are referred to as signal-generating cells, and they change their optical characteristics in response to changes in glucose concentration. The stem cells divide rapidly and as they differentiate they mostly loose the ability to differentiate. Therefore one first obtains a large number of non-differentiated cells and then differentiation occurs.

At this point, the desired cells are present in the initial set, and it is preferable to select the best cells for subsequent use. A first selection criterion for the cells is to select cells that fire rhythmically from the set, and this selection may be made by recording the electric activity of the using miniature electrodes onto which the cells adhere (e.g., gold electrodes about 20-50 microns in diameter). Standard electrophysiological amplifiers and display can be utilized for making this selection, as described in reference #11. After the cells that fire rhythmically are selected, a second selection criterion is preferably applied to the cells that passed the first selection phase. In the second selection phase, those cells that have acceptable functions are selected. This may be accomplished by measuring the firing rate function of individual cells when exposed to different levels of glucose. The firing rate may be measured using the same miniature electrodes mentioned above.

The firing rate of glucose sensitive cells at different glucose levels is depicted in FIG. 2. The number of action potentials or clusters thereof per time unit at different glucose concentrations are monitored in the relevant clinical concentration range (for example 2-20 mM), as described in reference #11. The cells that have acceptable functions are then selected for further use. Suitable selection criteria for "acceptability" include stability, repeatability, signal shape, and firing in the desired frequency range. Cells that have suitable functions are then stored, and the data representing the measured functions may optionally be stored for each of the cells that passed all the selection criteria.

At this point, the best signal-generating cells have been separated from the rest of the cells, and the next step is to aggregate batches of the best cells together to form clusters. This may be accomplished by expressing connexins in the selected cells and encouraging the formation of gap junctions to promote electric synchronization, as described in references #1 and 2.

Once the clusters are formed, additional phases of selection are preferably implemented to select the best clusters. A first selection criterion for the clusters is based on preferred size and shape. A preferred size is 100-200μ, and the preferred shape are the clusters that are closest to spherical or obloid. A second selection criterion for the clusters is how the cluster responds to different levels of glucose. This may be measured, for example, using the same electrodes described above in connection with the individual cells. Alternatively, it can be measured by optically measuring the clusters' response to different levels of glucose. The latter approach is advantageous because the responses of many clusters can be measured simultaneously by arranging the SIs in an array of tiny wells, capturing a video of the clusters as they are subjected to different glucose, and recording the optical reactions to those different glucose levels.

For each SI, the glucose-firing rate function is measured by exposing the SI to different levels of glucose and monitoring their firing rate at different glucose levels. The SIs with acceptable functions are selected and stored for subsequent use (e.g., in an incubator at 37° C., with $CO_2$, when necessary to maintain pH). Criteria for "acceptable" SIs are similar to the criteria discussed above for the individual cells, such stability, repeatability, signal shape, and firing in the desired frequency range. The data that corresponds to the stored SIs is also preferably stored in memory, as calibration data for subsequent use. This calibration data is referred to herein as the Dose-Response function, and the responses of the SIs (i.e., the clusters) to the various glucose levels is stored for subsequent use.

Note that multiple selection steps are described above—some at the cell level, and others at the SI level. But in alternative embodiments, one or more of these steps can be skipped, as long as the yield of usable SIs remains sufficiently high.

To utilize the stored SIs, the following steps may be performed. Each SI retrieved from storage is preferably accompanied by its associated data/documentation, i.e., the Dose-Response function. Optionally, the Dose-Response function of the SIs can be retested shortly prior to implantation to make sure that it has not changed and that the SI has not died. The SIs are preferably positioned such that each implanted SI ends up at a desired location following the implantation.

One way to achieve this implantation is by suspending the SIs in a semi-viscous biocompatible and bio-degradable fluid and then collecting each separately and sucking it a small distance into a transparent tube. By repeating this process the SIs can be aligned like a "string" and are sucked as such into small bore hypodermic needle. The "string" is then injected, preferably at a location that permits optical characteristics of the injected SIs to be detected from outside the subject's body after implantation. One particularly convenient location for human subjects is subcutaneously at the palmer side of the forearm. For animals, the most convenient location may vary depending on the species.

A number of SIs, e.g., between 2 and 20, and more preferably between 4 and 10, are placed in an injection medium with the distance between the individual SIs preferably between 0.2 and 2 mm. The SIs are lined up in selected positions in a Hypo needle. This positioning is designed to enable the injection of the SIs (for example while retreating the needle) such that the final distance between them in the tissue will be between 0.2 and 2 mm. The SIs are then injected subcutaneously and the positions of injection are noted. Optionally, a dye may be injected together with the SIs to help end users or health care professionals locate the place where the SIs have been implanted. Alternative implantation techniques will be readily apparent to persons skilled in the relevant arts.

Once introduced, the SIs maintain their proper function for at least 6 weeks (see reference #5). However, they have a tendency to migrate after 8-12 weeks (unpublished observations). While this migration might pose a problem for various other applications of engineered cells, it does not pose a serious problem in the context of glucose sensors, as repeated SI injection every 4-6 weeks is acceptable in this application.

In alternative embodiments, the SIs may be implemented as cultures on a biocompatible matrix having a surface to which cells readily adhere. Optionally, the matrix may be slowly degradable. Such a matrix should not interfere with nutrient diffusion and therefore can be made of a porous mass, such as those used in slow release drug pellets, a conglomerate of strings, etc.

When the SIs are implanted in the forearm, the sensors and their electronic and processing systems can be mounted on a device that is worn on the wrist like a watch, secured by a band in the vicinity of the SIs.

Figure 1B:
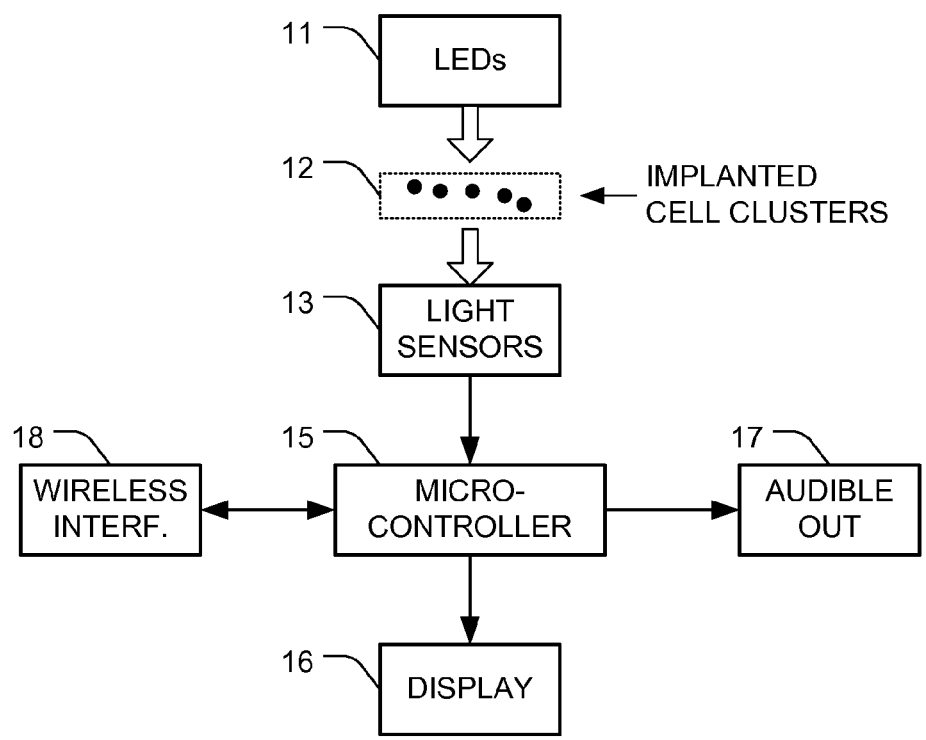
FIG. 1B is a block diagram of the FIG. 1A embodiment.

FIG. 1A is a schematic representation of a glucose measuring apparatus, referred to herein as a "Glucoter" in position on a subject's arm, and FIG. 1B is a block diagram of the same device. The lower face of the Glucoter preferably has optical sensors 13 (e.g., photodiodes, phototransistors, or arrays of sensors like CCDs or CMOS images) that sense optical changes in the SIs, and a light source (e.g., LEDs 11 at the appropriate wavelength) aimed to provide any necessary illumination. The sensors 13 detect the reflected illumination that bounces back off the SIs 12 and convert the optical signals into electric signals that are fed to amplifiers and/or A/D converters (not shown) that are designed accept signals from whichever type of sensor is used and convert those signals into a format that can be accepted by the microcontroller 15. The microcontroller 15 preferably includes enough memory and I/O circuits to perform all the functions described herein. In alternative embodiments, the integrated microcontroller 15 may be replaced with a microprocessor and separate memory and interface circuits (not shown).

After the SIs 12 are implanted (e.g., in the subject's arm 10), the Glucoter is positioned so that the illumination 11 and the sensors 13 in the Glucoter are aimed at the implanted SIs 12 by fastening the case 20 onto the subject's arm 10 right over the implanted SIs 12 using a strap 19 or other suitable fastener. The Glucoter is then activated. The calibration curves that were previously stored for each of the SIs that are implanted in the subject are loaded into the Glucoter's memory, e.g., via the wireless interface 18. Suitable memory types for storing the calibration data include flash memory and RAM that is maintained by a battery. Suitable protocols for the wireless interface 18 include Bluetooth. The Glucoter can then be used to determine the glucose level in the subject by monitoring changes in the optical properties of the implanted SIs, using the calibration curves for each of the SIs that have been implanted in the subject.

Changes in the optical properties are preferably recorded separately from each SI. The optical signals picked up by the sensors are amplified, digitized, processed (e.g., by a DSP) using suitable electronics and software (e.g., a suitably programmed microprocessor or DSP) to determine the glucose concentration from the signals arriving from the sensors. The translation of the optical signals to glucose concentration may be carried out by analyzing the signal frequency and shape as described for the electric signals as described in reference #11, because the shape of the optic signals matches the shape of the electrical signals depicted in FIG. 2 quite closely. Changes in the optical characteristics of the cell clusters that correspond to the responses of cells are identified based on changes in the amount of reflected illumination that was detected by the sensors 13.

The optical signals that measure the individual firing rate for each SI are mapped into glucose concentration by the corresponding individual calibration functions for the respective SI. The readings from each of the individual SIs may then be combined into an overall reading using any suitable algorithm such as a mean, median, or a mean taken after discarding the highest and lowest readings. The overall reading is then output. One way to implement this output is to display the computed glucose concentration on the digital display 16, which is preferably disposed on the upper face of the device. The display may be implemented using an LCD panel that preferably provides a numeric readout of the glucose level. An LED may also optionally be provided on the display, and the microcontroller 15 may be programmed to make the LED flash when the glucose level is dangerously high or low. Other data may also be displayed e.g., trends in the glucose level.

Optionally, the device can be configured to sound alarms via an audible output 17 (e.g., a speaker). Other options include controlling the output of an insulin (or other agent) pump or infusion. Optionally, the wireless interface 18 may transmit the data to a remote location such as a data logger or a remote medical surveillance center, etc. Alternatively, the data may be stored locally and retrieved in batch mode using a suitable wired interface (not shown) such as USB.

Figure 3A:
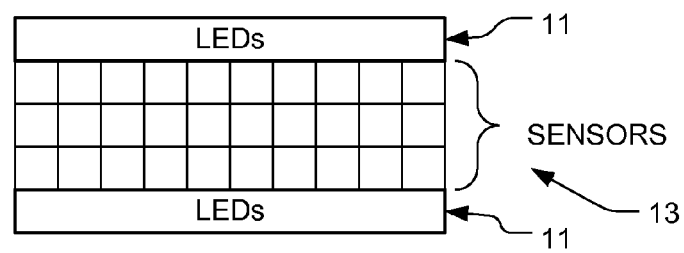
FIG. 3A depicts a first arrangement for the sensor and illumination elements.

FIG. 3A depicts a first arrangement for the sensor and illumination elements. This configuration uses a rectangular array of sensors 13. Note that while a 3 by 10 rectangular array of sensors is depicted, that number is only a representative example, and a different number of sensors and different geometries may be used. These sensors 13 can be individual photodiodes, or a CMOS or CCD based sensor similar to those used in digital cameras. When camera-type sensors are used, the pixels are much smaller, so multiple pixels are preferably logically combined into sensor blocks. For example, a 3,000 by 900 pixel array, which has a total of 2.7 Megapixels, may be logically divided into 30 blocks, with each block measuring 300 pixels by 300 pixels. Each of those blocks may then be treated as a single sensor element by averaging all the pixels in the block, which increases the signal with respect to using a single pixel. A block size of about 0.1 mm by 0.1 mm is suitable.

In this embodiment, the illumination elements 11 are positioned at the edges of the sensors 13, and each of these illumination elements 11 is preferably a linear array of LEDs. Single color LEDs (e.g., green or blue) or white LEDs may be used, but colors that are strongly attenuated by the skin or blood are preferably avoided.

Figure 3B:
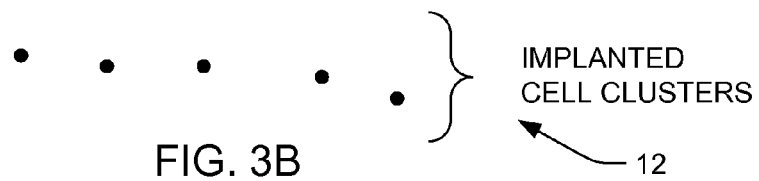
FIG. 3B depicts a typical arrangement for a set of implanted cell clusters.
Figure 3C:
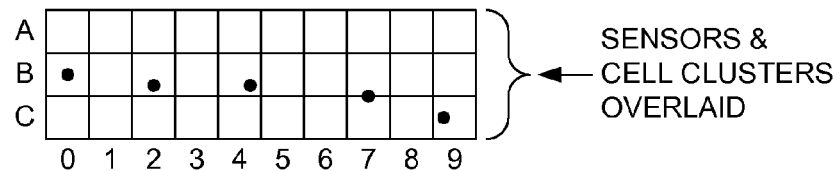
FIG. 3C depicts how the sensor arrangement of FIG. 3A lines up with the implanted cluster depicted in FIG. 3B.

FIG. 3B depicts a possible arrangement in space for a set of implanted cell clusters, i.e., a pattern where the implanted SIs 12 ended up after being implanted (with respect to each other). The sensors 13 should be positioned on the skin in the vicinity of the SIs 12 so that the SIs 12 lie within the perimeter of the sensor area. When a dye (e.g., color or fluorescent) was implanted with the SIs, it will be easier to align the sensors 13 with the SIs. FIG. 3C depicts how the sensor arrangement of FIG. 3A might line up with the implanted cluster of SIs 12 depicted in FIG. 3B when the sensors 13 are placed on the skin. The sensors 13 are preferably held in position by a strap 19 (shown in FIG. 1A).

Figure 4:
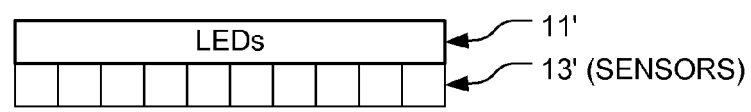
FIG. 4 depicts a second arrangement for the sensor and illumination elements.

FIG. 4 depicts an alternative arrangement for the sensor and illumination elements, which has only one row of sensor blocks 13' and one illumination element 11'. This embodiment will be less expensive to make because it has fewer components, but will have to be more carefully aligned with the implanted SIs 12 in order to work properly. Other numbers of rows may be used, e.g., 2 rows. A variety of other topologies for the sensor and illumination can be readily envisioned, including topologies where the illumination elements are interspersed in the middle of the sensor region.

The operation of the Glucoter will now be described in greater detail. Once the Glucoter is in position, the illumination is turned on and each of the sensors searches for activity. If a sensor happens to be in the vicinity of an SI, that sensor will detect optical signals that correspond to the "firing" of the cells in the SI. These signals will resemble the signals shown in FIG. 2. Based on the detected activity, the Glucoter notes which of the sensors is in the vicinity of an SI, and preferably forms a map that associates each SI with a given sensor element. The sensors that are not in the vicinity of an SI can be ignored during future operation of the device, until the device is repositioned. Note that since the Glucoter preferably has data for each of the SIs that was implanted, and the sequence of implantation is documented and reported to the Glucoter, the Glucoter can identify which SI is which one is which based on its position in the line. It is preferable to implant the SIs sufficiently far away from each other so that signals from two SIs will not arrive at the same sensor, which might confuse the calibration curves.

The glucose Dose-Response function (i.e., the calibration data) previously obtained for each SI, as described above, is then be assigned to a specific SI and the sensor that happens to be located in the vicinity of the SI. These sensor+SI pairs are used for future measurements. For each sensor+SI pair, the amplification gain and filtration for optimal signal recognition may be adjusted based on the calibration data. The signals from each SI are measured and stored.

The firing rate (which correlates to the glucose level, as depicted in FIG. 2) for each SI is measured over a period M. (M may be a predetermined period, e.g., one minute, or may be changed on a per-subject basis based on variability statistics.) The firing rate is then mapped onto a glucose level for each SI by using its calibration curve from the corresponding point on the Dose-Response function for the respective SI.

Optionally, the device may be recalibrated after it is activated. One suitable recalibration approach is to measure the subject's basal glucose level using a blood test, and input the results of the blood test to the Glucoter using, e.g., the wireless interface 18. The glucose level of the subject is then changed (e.g., by having the subject drink a known quantity of glucose or by intravenous infusion of glucose), additional blood tests are performed, and the results of the blood tests are input to the Glucoter (e.g., using the wireless interface 18). The readings obtained by the Glucoter are then compared to the input blood test readings. Any offset between the glucose readings obtained by the Glucoter using each of the individual SIs and the glucose levels measured in the blood are stored and used to calibrate future readings obtained from each of the individual SIs. The readings from each of the individual SIs, adjusted by this recalibration procedure, may then be combined into an overall reading using any suitable algorithm such as a mean, median, or a mean taken after discarding the highest and lowest readings.

When the readings that are obtained using a particular SI deviate too far from the results obtained using a blood test, or if the reading from a particular SI appear to be erratic or unstable, it can be an indication that that particular SI is no longer functioning properly. When that happens, the Glucoter is preferably programmed to store an indication that that particular SI is no longer functional, and to ignore that particular SI in the future.

One alternative to the LSG approach described above is the Dye-Coupled Generators (DCG) approach: In this embodiment, Generator cells incorporating in their outer membrane voltage sensitive dyes. These dyes emit flashes of light in response to membrane potential changes, or in response to the intracellular Ca ion concentration changes that accompany the action potentials. In some embodiments, the source of these voltage sensitive dyes can be the external medium, as described in reference #14, identified below. In alternative embodiments, they could be expressed within the cells by appropriate genetic induction. A sensor that senses the voltage variations is then positioned in the vicinity of the SIs. DCG can be advantageous because it produces relatively large signals while only requiring the addition of dyes. Such dyes fluoresce when incorporated into cells. They are known to generate light of sufficient intensity to be picked up at the skin surface of animals such as mice, as described in references #22-26, identified below.

Another alternative to the LSG approach is Muscle-Coupled Generators (MCG). With MCG, Generator cells coupled by means of gap junctions to contractile cells (myocytes) such that each spike generated in the SIs elicits a corresponding muscular contraction or twitch. These contractions act like a biological amplifier that makes the signal easier to detect. Those contractions or twitches can then be monitored and quantized. MCG can be advantageous because muscle contraction produces relatively large optic signals that can be detected at a distance. However, even when their origin is hMSCs, the cells that differentiate into myocytes are expected to lose their immunoprivileged status. This problem can be overcome by using autologous contractile cells from the hair follicles of the subject as previously described reference #10, identified below.

Another alternative to the LSG approach is Glucose Transporter Coupled Generators (GTCG) where the front end of a glucose transporter is coupled to the back end of a measureable signal transduction pathway like the beta receptor. In this alternative, it becomes possible to use cardiomyocyte pacing as an in vivo sensor for glucose levels as described in references #8 and 9, identified below.

The following references provide relevant background information:

Reference #1: Valiunas V, Doronin S, Valiuniene L, Potapova I, Zuckerman J, Walcott B, Robinson R B, Rosen M R, Brink P R, Cohen I S: Human mesenchymal stem cells make cardiac connexins and form functional gap junctions. J Physiol. 2004: 555: 617-626

Reference #2: Valiunas V, Polosina Y Y, Miller H, Potapova I A, Valiuniene L, Doronin S, Mathias R T, Robinson R B, Rosen M R, Cohen I S, Brink P R. Connexin-specific cell-to-cell transfer of short interfering RNA by gap junctions. J Physiol. 2005; 568:459-68.

Reference #3: Valiunas V, Kanaporis G, Valiuniene L, Gordon C, Wang H Z, Li L, Robinson R B, Rosen M R, Cohen I S, Brink P R. Coupling an HCN2-expressing cell to a myocyte creates a two-cell pacing unit. J Physiol. 2009:587: 5211-26

Reference #4: Potapova I, Plotnikov A, Lu Z, Danilo P Jr, Valiunas V, Qu J, Doronin S, Zuckerman J, Shlapakova I N, Gao J, Pan Z, Herron A J, Robinson R B, Brink P R, Rosen M R, Cohen I S: Human mesenchymal stem cells as a gene delivery system to create cardiac pacemakers. Circ Res 94:952-959, 2004.

Reference #5: Plotnikov A N, Shlapakova I, Szabolcs M J, Danilo Jr P, Lorell B H, Potapova I A, Lu Z, Rosen A B, Mathias R T, Brink P R, Robinson R B, Cohen I S, Rosen M R. Xenografted adult human mesenchymal stem cells provide a platform for sustained biological pacemaker function in canine heart. Circulation 2007; 116:706-713.

Reference #6: Aggarwal S, Pittenger M F. Human mesenchymal stem cells modulate allogeneic immune cell responses. Blood. 2005; 105:1815-1822

Reference #7: Rosen M R. Are Stem Cells Drugs? The regulation of stem cell research and development. Circulation. 2006; 114:1992-2000.

Reference #8: Christini D J, Walden J, Edelberg J M. Direct biologically based biosensing of dynamic physiological function. Am J Physiol Heart Circ Physiol. 2001:280: H2006-10

Reference #9: Edelberg J M, Jacobson J T, Gidseg D S, Tang L, Christini D J. Enhanced myocyte-based biosensing of the blood-borne signals regulating chronotropy. J Appl Physiol. 2002:92:581-585

Reference #10: Novak A, Shtrichman R, Germanguz I, Segev H, Zeevi-Levin N, Fishman B, Mandel Y E, Barad L, Domev H, Kotton D, Mostoslaysky G, Binah O, Itskovitz-Eldor J. Enhanced reprogramming and cardiac differentiation of human keratinocytes derived from plucked hair follicles, using a single excisable lentivirus. Cell Reprogram. 2010; 12:665-78

Reference #11: Palti Y., David G. B., Lachov E., Mika Y. H. and Schatzberger R. Islets of Langerhans generate electric activity modulated by glucose concentration. Diabetes 45: 595-601 (1996)

Reference #12: Cohen L. B. Changes in Neuron Structure During Action Potential Propagation and Synaptic Transmission. Physiological Reviews 1973; 53:373-418

Reference #13: Benedikt W. Graf, Tyler S. Ralston, Han-Jo Ko, and Stephen A. Boppart Detecting intrinsic scattering changes correlated to neuron action potentials using optical coherence imaging. Optics Express 2009; 17: 13447-13457

Reference #14: B. J. Baker, E. K. Kosmidis, D. Vucinic, C. X. Falk, L. B. Cohen, M. Djurisic, and D. Zecevic Imaging brain activity with voltage- and calcium-sensitive dyes. Cell. Mol. Neurobiol. 2005; 25:245-282

Reference #15: R. A. Stepnoski, A. LaPorta, F. Raccuia-Behling, G. E. Blonder, R. E. Slusher, and D. Kleinfeld Noninvasive detection of changes in membrane potential in cultured neurons by light scattering. Proc. Natl. Acad. Sci. U.S.A. 1991; 88: 9382-386

Reference #16: K. Holthoff and O. W. Witte, Intrinsic optical signals in rat neocortical slices measured with near-infrared dark-field microscopy reveal changes in extracellular space 1996; J. Neurosci. 16: 2740-2749

Reference #17: R. U. Maheswari, H. Takaoka, H. Kadono, R. Homma, and M. Tanifuji, Novel functional imaging technique from brain surface with optical coherence tomography enabling visualization of depth resolved functional structure in vivo 2003; J. Neurosci. Methods 124: 83-92

Reference #18: T. Akkin, D. P. Dave, T. E. Milner, and H. Rylander 2004; Detection of neural activity using phase-sensitive optical low-coherence reflectometry Opt. Express 12: 2377-2386

Reference #19: T. Akkin, C. Joo, and J. F. de Boer, Depth-resolved measurement of transient structural changes during action potential propagation 2007; Biophys. J. 93: 1347-1353

Reference #20: V. J. Srinivasan, M. Wojtkowski, J. G. Fujimoto, and J. S. Duker, In vivo measurement of retinal physiology with high-speed ultrahigh-resolution optical coherence tomography 2006; Opt. Lett.: 31, 2308-2310

Reference #21: J. F. de Boer, T. E. Milner, M. J. van Gernert, and J. S. Nelson Two-dimensional birefringence imaging in biological tissue by polarization-sensitive optical coherence tomography 1997; Opt. Lett.: 22, 934-936

Reference #22: Akkin T, Landowne D, Sivaprakasam A. Detection of Neural Action Potentials Using Optical Coherence Tomography: Intensity and Phase Measurements with and without Dyes. 2010; Front Neuroenergetics:6, 2-22

Reference #23: Li Y, Gonzalez S, Terwey T H, Wolchok J, Li Y, Aranda I, Toledo-Crow R, Halpern A C Dual mode reflectance and fluorescence confocal laser scanning microscopy for in vivo imaging melanoma progression in murine skin. 2005; Invest Dermatol. 125:798-804.

Reference #24: Shan Jiang, Muthu Kumara Gnanasammandhan and Yong Zhang Optical imaging-guided cancer therapy with fluorescent nanoparticles 2010; J. R. Soc. Interface 7: 3-18

Reference #25: Xiaoxiao He, Kemin Wang, Zhen Cheng 2010; In vivo near□infrared fluorescence imaging of cancer with nanoparticle□based probes 2010; Wiley Interdisciplinary Reviews: Nanomedicine and Nanobiotechnology Volume 2:349-366

Reference #26: Xiaoxiao He, Kemin Wang, Zhen Cheng In vivo near□infrared fluorescence imaging of cancer with nanoparticle□based probes, Advanced Review 2010; WIREs Nanomed Nanobiotechnol: 2 349-366

Reference #27: James R. Mansfield, Clifford C. Hoyt, Peter J. Miller, and Richard M. Levenson Distinguished photons: increased contrast with multispectral in vivo fluorescence imaging 2005; BioTechniques:39: S33-S37

Reference #28: Wild, S, Roglic, G, Green, A, et al. Global prevalence of diabetes: estimates for the year 2000 and projections for 2030. Diabetes Care 2004; 27:1047.

Reference #29: Intensive blood-glucose control with sulphonylureas or insulin compared with conventional treatment and risk of complications in patients with type 2 diabetes (UKPDS 33). UK Prospective Diabetes Study (UKPDS) Group. Lancet 1998; 352:837.

Reference #30: Moss, S E, Klein, R, Klein, B E. The incidence of vision loss in a diabetic population. Ophthalmology 1988; 95:1340.

Reference #31: Humphrey, L L, Ballard, D J, Frohnert, P P, et al. Chronic renal failure in non-insulin-dependent diabetes mellitus. A population-based study in Rochester, Minn. Ann Intern Med 1989; 111:788.

Reference #32: Lakshmi Kiran Chelluri, Ravindranath Kancherla, Nagaraju Turlapati, Sathish Vemuri, Tanya Debnath, Praveen Kumar, Syed Sultan Beevi, Ratnakar Suguna Kamarajul Improved differentiation protocol of rat bone marrow precursors to functional islet like cells: Stem Cell Studies 2011; 1:e5 pp 36-41.

While the present invention has been disclosed with reference to certain embodiments, numerous modifications, alterations, and changes to the described embodiments are possible without departing from the sphere and scope of the present invention, as defined in the appended claims. For example, instead of measuring glucose, other chemicals may be measured by replacing the glucose-sensitive cells described above with cells that respond those other chemicals. Numerous other alternatives can also be readily envisioned. Accordingly, it is intended that the present invention not be limited to the described embodiments, but that it has the full scope defined by the language of the following claims, and equivalents thereof.

What is claimed is:

1. A method of monitoring a glucose level in a live subject, comprising the steps of:
   obtaining at least one stem cell from the subject;
   processing the at least one stem cell into a plurality of signal-generating cells that change their optical characteristics in response to changes in glucose concentration;
   forming the plurality of signal-generating cells into at least two cell clusters;
   determining, prior to implantation, for each of the at least two cell clusters, calibration data that relates responses of the respective cell cluster to glucose levels;
   implanting the at least two cell clusters into in the subject's body at locations that permit optical characteristics of the at least two cell clusters to be detected from outside the subject's body after implantation;
   illuminating the at least two implanted cell clusters;
   detecting reflected illumination from each of the at least two cell clusters;
   identifying changes in the optical characteristics of the cell clusters that correspond to the responses of the cell clusters, for each of the at least two cell clusters, based on changes in the amount of reflected illumination detected in the detecting step;
   mapping, for each of the at least two cell clusters, the identified change in optical characteristics to a glucose level based on the calibration data for the respective cell cluster; and
   outputting an indication of the glucose level in the subject based the glucose levels obtained in the mapping step.

2. The method of claim 1 wherein the obtaining step comprises obtaining at least one stem cell from a hair follicle of the subject.

3. The method of claim 1 wherein, in the processing step, the at least one stem cell is processed to yield a plurality of signal-generating cells with additional connexons in the cell membrane to promote synchronization.

4. The method of claim 1 wherein, in the forming step, the plurality of signal-generating cells are formed into cell clusters that are between 100 and 200 microns in diameter by collecting signal-generating cells into clumps.

5. The method of claim 1 wherein, in the determining step, calibration data that relate responses of the respective cell clusters to glucose levels are determined simultaneously for all the cell clusters by capturing a video of all the cell clusters and analyzing the video.

6. The method of claim 1 wherein, in the implanting step, a dye is implanted together with the cell clusters, wherein the dye is selected to make the locations of the cell cluster more visible.

7. The method of claim 1 further comprising the step of selecting the at least two cell clusters from a larger set of cell clusters by
   capturing a video of the larger set of cell clusters responding to changes in glucose levels,
   analyzing the video to determine which cell clusters in the larger set work well, and
   selecting cell clusters that work well for implantation in the subject.

8. The method of claim 1 further comprising the steps of:
   positioning an array of sensors elements in a vicinity of the cell clusters;
   monitoring the illumination reflected from the sensor elements;
   identifying, based on the monitored illumination, which sensor element in the array provides a strong return for each of the at least two cell clusters;
   storing an indication of which sensor elements were identified in the identifying step; and
   using the stored indication to select which sensor elements should be used for subsequent determinations of glucose levels.

9. An apparatus for monitoring a glucose level in a live subject into which at least two cell clusters have been implanted at locations that permit optical characteristics of the at least two cell clusters to be detected from outside the subject's body after implantation, the apparatus comprising:
   a light source that is oriented to shine illumination onto the at least two implanted cell clusters when the apparatus is fastened in place in a vicinity of the at least two implanted cell clusters;
   a memory that holds calibration data for the at least two implanted cell clusters that relates responses of each cell cluster to glucose levels, wherein the calibration data is obtained prior to implantation of the cell clusters;
   an array of light sensors that are oriented to receive illumination reflected from the at least two implanted cell clusters when the apparatus is fastened in place, and generate intensity data; and
   a processor that is programmed to perform the steps of (a) inputting the intensity data, (b) identifying activity in the cell clusters, for each of the at least two implanted cell clusters, based on changes the intensity data, (c) mapping, for each of the at least two implanted cell clusters, the identified activity to a glucose level based on the calibration data stored in the memory, and (d) outputting an indication of the glucose level in the subject based a result of the mapping.

10. The apparatus of claim 9, further comprising a fastener that is configured to hold the apparatus in place on the subject's body in the vicinity of the at least two implanted cell clusters.

11. The apparatus of claim 9, wherein the processor is further programmed to perform the steps of (e) identifying, based on the inputted intensity data, which elements in the array of light sensors provides a strong return for each of the at least two implanted cell clusters, and (f) using the identified elements to make subsequent determinations of glucose levels.

12. A method of monitoring a constituent level in a live subject, comprising the steps of:
   obtaining at least one stem cell from the subject;
   processing the at least one stem cell into a plurality of cells that change their optical characteristics in response to a level of the constituent;
   forming the plurality of responsive cells into at least two cell clusters;
   determining, prior to implantation, for each of the at least two cell clusters, calibration data that relates responses of the respective cell cluster to constituent levels;
   implanting the at least two cell clusters into in the subject's body at locations that permit optical characteristics of the at least two cell clusters to be detected from outside the subject's body after implantation;
   illuminating the at least two implanted cell clusters;
   detecting reflected illumination from each of the at least two cell clusters;

identifying changes in the optical characteristics of the cell clusters that correspond to the responses of the cell clusters, for each of the at least two cell clusters, based on changes in the amount of reflected illumination detected in the detecting step;

mapping, for each of the at least two cell clusters, the identified change in optical characteristics to a constituent level based on the calibration data for the respective cell cluster; and outputting an indication of the constituent level in the subject based the constituent levels obtained in the mapping step.

13. The method of claim 12 wherein the obtaining step comprises obtaining at least one stem cell from a hair follicle of the subject.

14. The method of claim 12 wherein, in the processing step, the at least one stem cell is processed to yield a plurality of cells with additional connexons in the cell membrane to promote synchronization.

15. The method of claim 12 wherein, in the determining step, calibration data that relate responses of the respective cell clusters to constituent levels are determined simultaneously for all the cell clusters by capturing a video of all the cell clusters and analyzing the video.

16. The method of claim 12 wherein, in the implanting step, a dye is implanted together with the cell clusters, wherein the dye is selected to make the locations of the cell cluster more visible.

17. The method of claim 12 further comprising the step of selecting the at least two cell clusters from a larger set of cell clusters by
    capturing a video of the larger set of cell clusters responding to changes in constituent levels,
    analyzing the video to determine which cell clusters in the larger set work well, and
    selecting cell clusters that work well for implantation in the subject.

18. The method of claim 12 further comprising the steps of:
    positioning an array of sensors elements in a vicinity of the cell clusters;
    monitoring the illumination reflected from the sensor elements;
    identifying, based on the monitored illumination, which sensor element in the array provides a strong return for each of the at least two cell clusters;
    storing an indication of which sensor elements were identified in the identifying step; and
    using the stored indication to select which sensor elements should be used for subsequent determinations of constituent levels.

19. An apparatus for monitoring a constituent level in a live subject into which at least two cell clusters have been implanted at locations that permit optical characteristics of the at least two cell clusters to be detected from outside the subject's body after implantation, the apparatus comprising:
    a light source that is oriented to shine illumination onto the at least two implanted cell clusters when the apparatus is fastened in place in a vicinity of the at least two implanted cell clusters;
    a memory that holds calibration data for the at least two implanted cell clusters that relates responses of each cell cluster to constituent levels, wherein the calibration data is obtained prior to implantation of the cell clusters;
    an array of light sensors that are oriented to receive illumination reflected from the at least two implanted cell clusters when the apparatus is fastened in place, and generate intensity data; and
    a processor that is programmed to perform the steps of (a) inputting the intensity data, (b) identifying activity in the cell clusters, for each of the at least two implanted cell clusters, based on changes the intensity data, (c) mapping, for each of the at least two implanted cell clusters, the identified activity to a constituent level based on the calibration data stored in the memory, and (d) outputting an indication of the constituent level in the subject based a result of the mapping.

20. The apparatus of claim 19, further comprising a fastener that is configured to hold the apparatus in place on the subject's body in the vicinity of the at least two implanted cell clusters.

21. The apparatus of claim 19, wherein the processor is further programmed to perform the steps of (e) identifying, based on the inputted intensity data, which elements in the array of light sensors provides a strong return for each of the at least two implanted cell clusters, and (f) using the identified elements to make subsequent determinations of constituent levels.

* * * * *